(12) United States Patent
Yoo et al.

(10) Patent No.: US 10,475,260 B2
(45) Date of Patent: Nov. 12, 2019

(54) WEARABLE ELECTRONIC DEVICE HAVING USER IDENTIFICATION FUNCTION AND USER AUTHENTICATION METHOD

(71) Applicant: Samsung Electronics Co., Ltd., Suwon-si (KR)

(72) Inventors: Sungsik Yoo, Yongin-si (KR); Yongju Yu, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 78 days.

(21) Appl. No.: 14/757,649

(22) Filed: Dec. 23, 2015

(65) Prior Publication Data

US 2016/0189451 A1   Jun. 30, 2016

(30) Foreign Application Priority Data

Dec. 24, 2014   (KR) .......................... 10-2014-0188556

(51) Int. Cl.

| | | |
|---|---|---|
| *G07C 9/00* | (2006.01) | |
| *G06F 21/34* | (2013.01) | |
| *G06F 21/35* | (2013.01) | |
| *H04W 12/06* | (2009.01) | |
| *G06F 21/32* | (2013.01) | |
| *A61B 5/117* | (2016.01) | |
| *H04W 12/00* | (2009.01) | |

(Continued)

(52) U.S. Cl.
CPC .......... *G07C 9/00087* (2013.01); *A61B 5/117* (2013.01); *G06F 21/32* (2013.01); *G06F 21/34* (2013.01); *G06F 21/35* (2013.01); *H04L 63/0853* (2013.01); *H04L 63/0861* (2013.01); *H04W 12/003* (2019.01); *H04W 12/06* (2013.01); *A61B 5/0404* (2013.01); *A61B 5/04525* (2013.01); *A61B 5/681* (2013.01); *G07C 2009/00095* (2013.01)

(58) Field of Classification Search
None
See application file for complete search history.

(56) References Cited

U.S. PATENT DOCUMENTS

| | | |
|---|---|---|
| 5,807,267 A | 9/1998 | Bryars et al. |
| 7,171,259 B2 | 1/2007 | Rytky |

(Continued)

FOREIGN PATENT DOCUMENTS

WO   2014/089665 A1   6/2014

OTHER PUBLICATIONS

Communication w/ European Search Report dated Mar. 17, 2016 corresponding to European Patent Application No. 15202358.

(Continued)

*Primary Examiner* — Daniell L Negron
(74) *Attorney, Agent, or Firm* — Jefferson IP Law, LLP (57) ABSTRACT

An electronic device having user identification function and a user authentication method are provided. The electronic devices comprises: a body; a user identification unit that detects a body signal of the user and processes authentication of the user; an in-use detection unit that detects the body signal of the user and checks whether the user uses the electronic device; and a processor that authenticates the user according to detection signals of the user identification unit and the in-use detection unit.

12 Claims, 8 Drawing Sheets

(51) Int. Cl.
 A61B 5/00 (2006.01)
 H04L 29/06 (2006.01)
 *A61B 5/0404* (2006.01)
 *A61B 5/0452* (2006.01)

(56) References Cited

U.S. PATENT DOCUMENTS

| | | |
|---|---|---|
| 2005/0033991 A1* | 2/2005 | Crane .................. H04L 63/1433 726/4 |
| 2005/0071647 A1 | 3/2005 | Fujinuma |
| 2014/0085050 A1 | 3/2014 | Luna |
| 2014/0372762 A1 | 12/2014 | Flautner et al. |
| 2015/0028996 A1* | 1/2015 | Agrafioti .................. G06F 21/40 340/5.82 |
| 2015/0135310 A1 | 5/2015 | Lee |
| 2015/0366469 A1 | 12/2015 | Harris et al. |

OTHER PUBLICATIONS

Bionym: "nymi", Nov. 19, 2013 (Nov. 19, 2013), XP055195746, Retrieved from the Internet: URL:https://www.nymi.com/wp-content/uploads/2013/11/NymiWhitePaper-1.pdf [retrieved on Jun. 15, 2015].
Office Action dated Nov. 30, 2016 corresponding to European Patent Application No. 15 202 358.6.

* cited by examiner

WEARABLE ELECTRONIC DEVICE HAVING USER IDENTIFICATION FUNCTION AND USER AUTHENTICATION METHOD

RELATED APPLICATION(S)

The present application is related to and claims benefit under 35 U.S.C. § 119(a) of Korean patent application filed on Dec. 24, 2014 in the Korean Intellectual Property Office and assigned Serial number 10-2014-0188556, the entire disclosure of which is hereby incorporated by reference.

BACKGROUND

The present disclosure relates to an electronic device having a user identification function and a user authentication method.

In recent years, in various fields, for example, the inclusion of a payment and/or an entrance service in the work field, e-commerce, e-banking, e-investing, e-data protection, remote access to a resource, e-transaction, work security, a theft prevention device, identification of a criminal, security entry, and entry registration, the importance of the recognition of an identity, such as the identification and verification of a personal identity, has increased.

The recognition of a personal identity may use electro-biometric identification and a verification system independently, or may be combined with a technology, such as a smart key, an encryption key, or a digital signature.

However, a separate user identification means, such as a password, a personal identification number (PIN) or card, or an accredited certificate is necessary for the recognition of the user. The password should be changed regularly in order to maintain security, which is a considerable burden to the user.

In a wearable electronic device that is mounted on a wrist of the user in the form of a watch or a band (e.g., in an existing smart watch as the electronic device), a method of authenticating the user through electrocardiogram (ECG) recognition has been suggested.

However, the conventional electronic device should sense an electrocardiogram whenever the user is authenticated.

SUMMARY

Therefore, the present disclosure has been made in an effort to solve the above-mentioned problems, and provides an electronic device that can authenticate the user as long as it is worn by the user, without using a separate user identification means, by mounting both a user identification sensor and a wearing state detection sensor on the electronic device, thereby maintaining the authentication effect, and provides a user authentication method.

The present disclosure also provides an electronic device that can be associated with various applications without performing an additional user authentication, and a user authentication method.

In accordance with an aspect of the present disclosure, an electronic device comprises: a user identification unit that detects a body signal of the user and processes authentication of the user; an in-use detection unit that detects the body signal of the user and checks whether the user uses the electronic device; and a processor that authenticates the user according to the body signal detected by the user identification unit and the body signal detected by the in-use detection unit.

The user identification unit may comprise an ECG sensor that identifies the user through ECG sensing.

The in-use detection unit may comprise a heart rate monitor (FIRM) sensor that detects a wearing state of the electronic device by the user.

The electronic device may comprise a body. The ECG sensor may comprise a first identification sensor and a second identification sensor, and the first and second identification sensors may be attached to different surfaces of the body.

The first identification sensor may generate a waveform according to an ECG pattern of heartbeats of the user, and the second identification sensor may generate a waveform according to an ECG pattern when the user makes various payments or performs an authentication in a login process.

The first identification sensor may be located in a button on the body to be operated by pushing the button, and completes a human body communication loop.

The HRM sensor may detect a wearing state of the electronic device by the user in a photoplethysmography (PPG) method.

The processor may record a waveform detected through the user identification unit, compare the waveform with an ECG pattern of the user yielding in a comparison result, the ECG pattern being registered in advance, by using an ECG pattern analysis solution, and process a user authentication for the electronic device by identifying the user according to the comparison result.

The processor may comprise a memory that stores authentication contents of the user through ECG sensing.

The electronic device further may comprise: a body and a coupling detection sensor that detects whether the body is maintained at a wearing location of the user.

The processor may eliminate the authentication contents of the user through ECG sensing stored in the memory according to a detection signal of at least one of the coupling detection sensor and the in-use detection unit.

The authentication of the user may be used in association with an application, if the in-use detection unit of the electronic device determines that the electronic device is being worn by the user after the processor authenticates the user resulting in an authentication of the user.

The electronic device may further comprise a body. The body further may comprise a wrongful use prevention sensor in a band that is located at a wearing position of the user.

The wrongful use prevention sensor may be a conductive body that is embedded in a band.

In accordance with another aspect of the present disclosure, a user authentication method for use with an electronic device having a body may comprise: registering an ECG pattern of a user resulting in a registered ECG pattern; sensing an ECG pattern of the user; comparing the registered ECG pattern and the ECG pattern of the user sensed, and identifying the user; if the the registered ECG pattern coincides with the ECG pattern of the user sensed based on the identification, authenticating the user and storing authentication information; and checking a wearing state of the body.

The authentication information stored may be discarded, if the wearing state of the body is released or the body is not worn.

The authentication of the user may be used in association with an application, if the wearing state of the body is identified.

The user may be identified by comparing the registered ECG pattern of the user with the ECG pattern of the user sensed using an ECG pattern analysis solution.

When the wearing state of the body is identified, the stored authentication may be automatically discarded via detecting a wrongful use of the body by a third person.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE EXEMPLARY EMBODIMENTS

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications can be made to the various embodiments described herein without departing from the scope and spirit of the present disclosure. In addition, descriptions of well-known functions and constructions may be omitted for clarity and conciseness.

The terms and words used in the following description and claims are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used in embodiments of the present disclosure, the expression "include" or "may include" or "can include" refers to the existence of a corresponding function, operation, or constituent element, and does not limit one or more additional functions, operations, or constituent elements. Further, as used in embodiments of the present disclosure, the term, such as "include" or "have" may be construed to denote a certain characteristic, number, operation, constituent element, component or a combination thereof, but may not be construed to exclude the existence of or a possibility of addition of one or more other characteristics, numbers, operations, constituent elements, components or combinations thereof.

As used in embodiments of the present disclosure, the expression "and/or" includes any or all combinations of words enumerated together. For example, the expression "A or B" or "at least one of A and B" may include A, may include B, or may include both A and B.

While expressions including ordinal numbers, such as "first" and "second", as used in the present disclosure may modify various constituent elements, such constituent elements are not limited by the above expressions. For example, the above expressions may not indicate a specific order and/or relative importance of the corresponding constituent elements. The above expressions may be used merely for the purpose of distinguishing a constituent element from other constituent elements. For example, a first user device and a second user device indicate different user devices although both are user devices. For example, a first constituent element may be termed a second constituent element, and likewise a second constituent element may also be termed a first constituent element without departing from the scope of the present disclosure.

When a first component is referred to as being "connected" or "accessed" to a second component, it should be understood that the first component may be directly connected or accessed to the second component, but also that a third component may be interposed between the first and second components. Contrarily, when the first component is referred to as being "directly connected" or "directly accessed" to the second component, it should be understood that there is no other component between the first component and the second component.

In various embodiments of the present disclosure, an electronic device may be a device that involves a communication function. Accordingly, an electronic device may be, for example, a smart phone, personal computer (PC), a tablet PC, a mobile phone, a video phone, an e-book reader, a desktop PC, a laptop PC, a netbook computer, a Personal Digital Assistant (PDA), a Portable Multimedia Player (PMP), a Moving Picture Experts Group (MPEG-1 or MPEG-2) Audio Layer-3 (MP3) player, a portable medical device, a digital camera, or a wearable device (e.g., a Head-Mounted Device (HMD), such as electronic glasses, electronic clothes, an electronic bracelet, an electronic necklace, electronic tattoos, an electronic appcessory, a smart watch, and the like).

Figure 1:
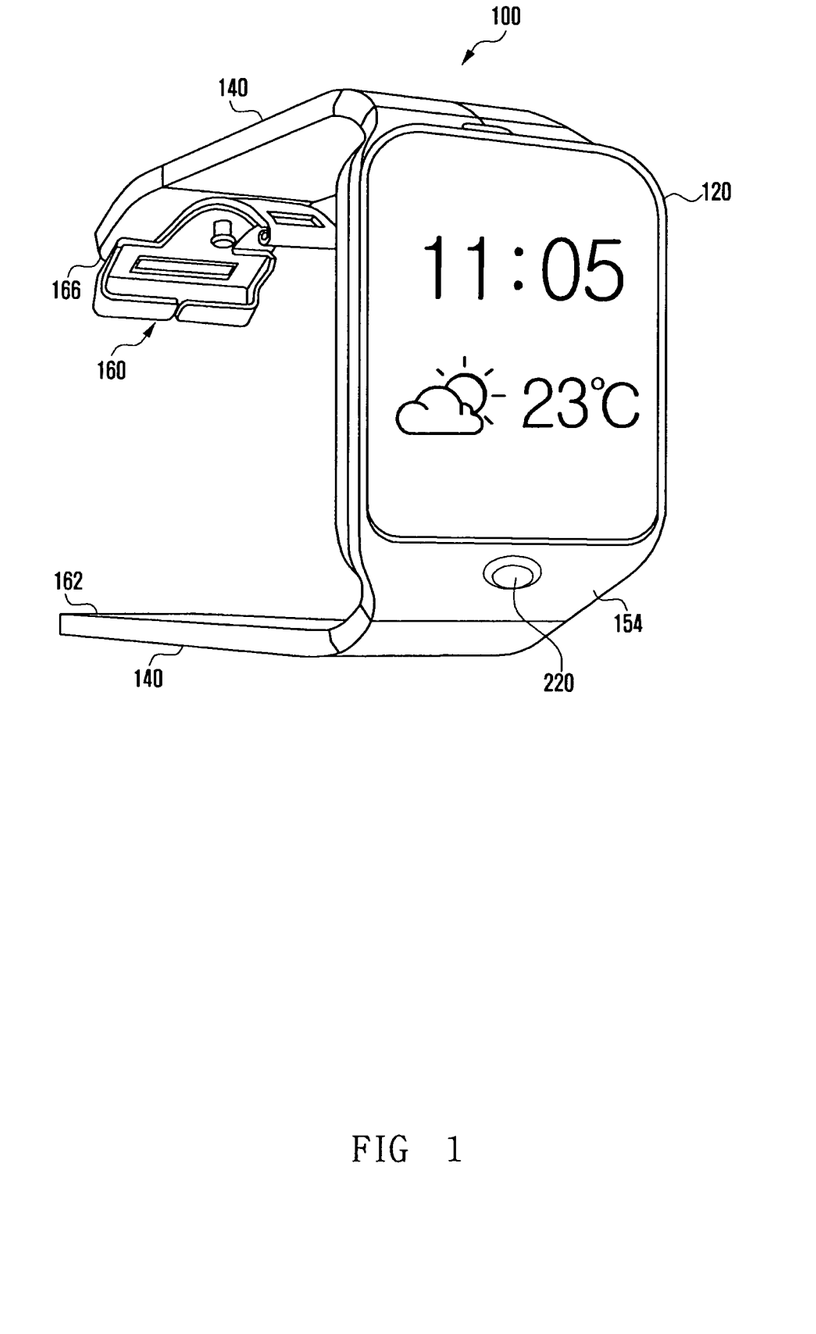
FIG. 1 is a perspective view illustrating a front surface of an electronic device that has a user identification function according to various embodiments of the present disclosure.
Figure 2:
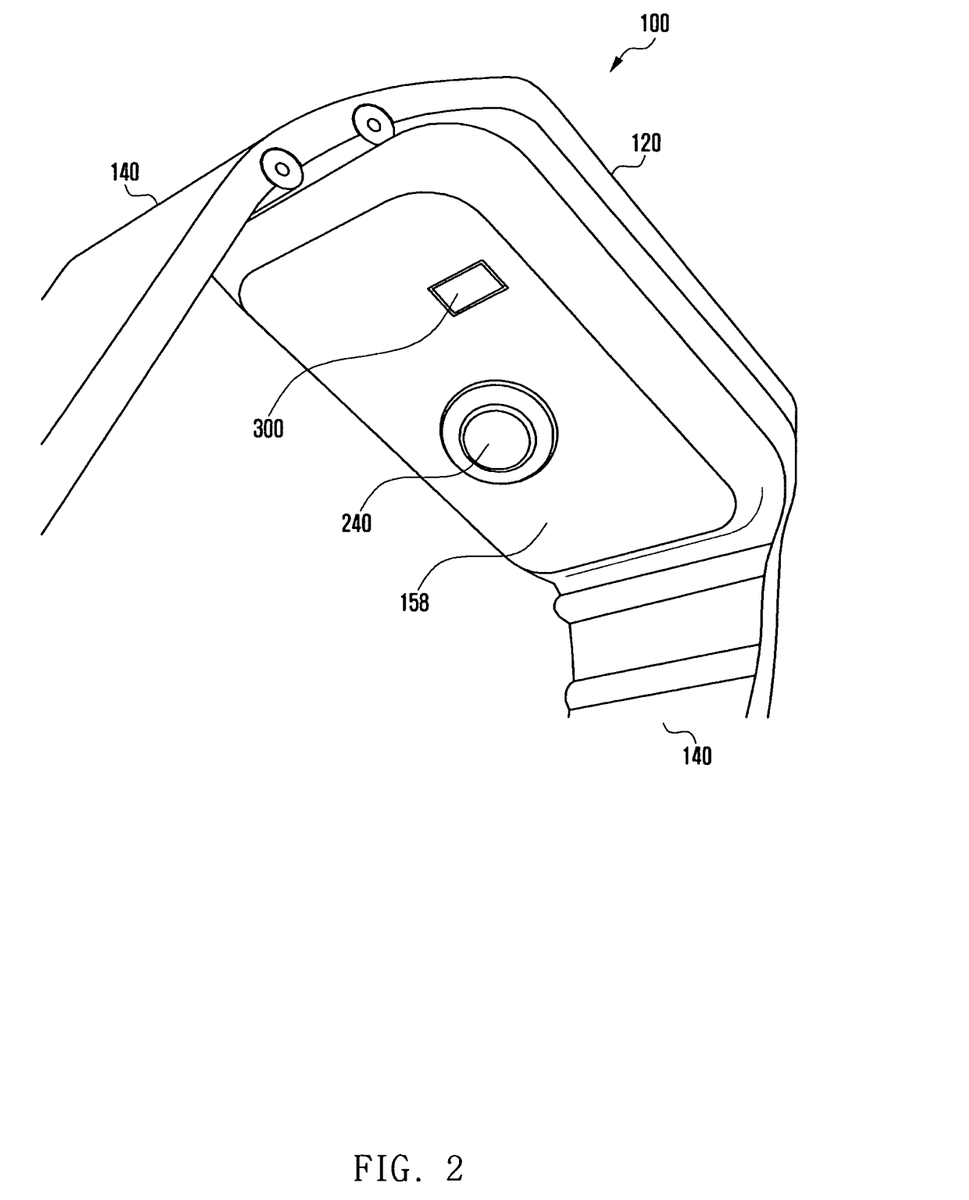
FIG. 2 is a perspective view illustrating a rear surface of the electronic device of FIG. 1.
Figure 3:
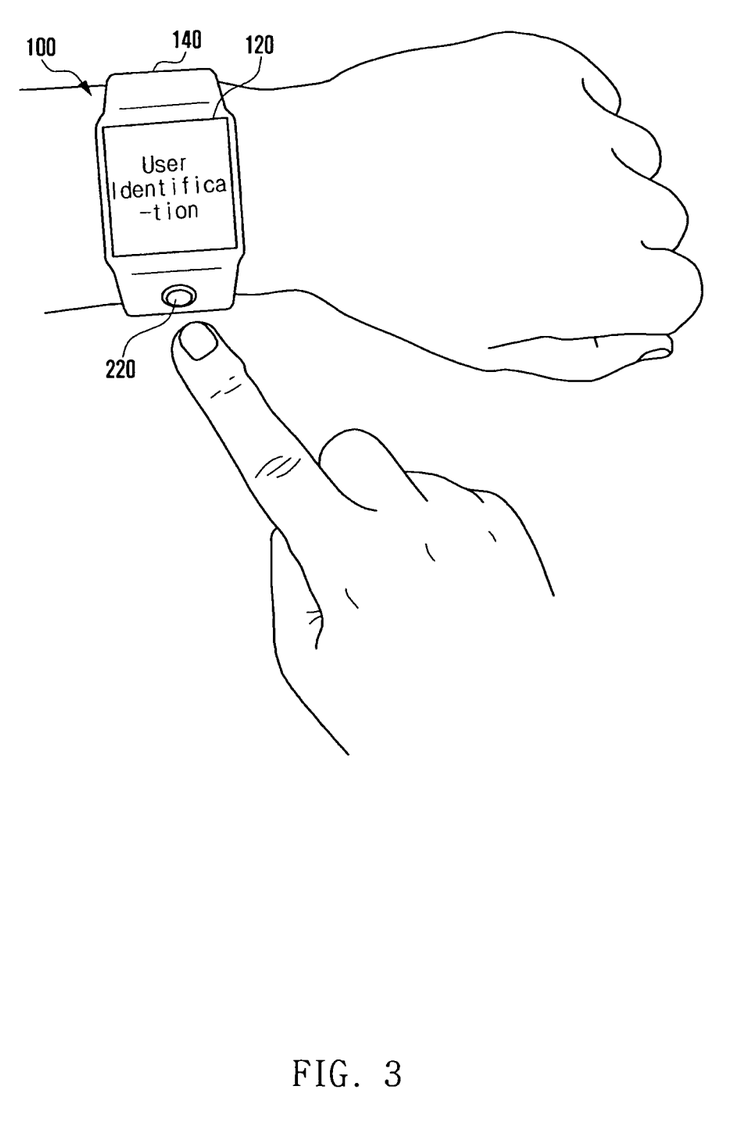
FIG. 3 is a schematic diagram illustrating a wearing state of an electronic device according to various embodiments of the present disclosure.

FIGS. 1 and 2 illustrate an electronic device 100 that has a user identification function according to various embodiments of the present disclosure. FIG. 3 illustrates a wearing state of the electronic device 100 of FIG. 1.

The electronic device 100 that has a user identification function according to various embodiments of the present disclosure is, for example, a smart watch, and includes a housing or body 120, a band 140 for mounting or securing the body 120 on a wrist of the user, and a buckle assembly 160 that couples opposite ends of the band 140 to maintain a desired mounting position of the body 120.

Figure 5:
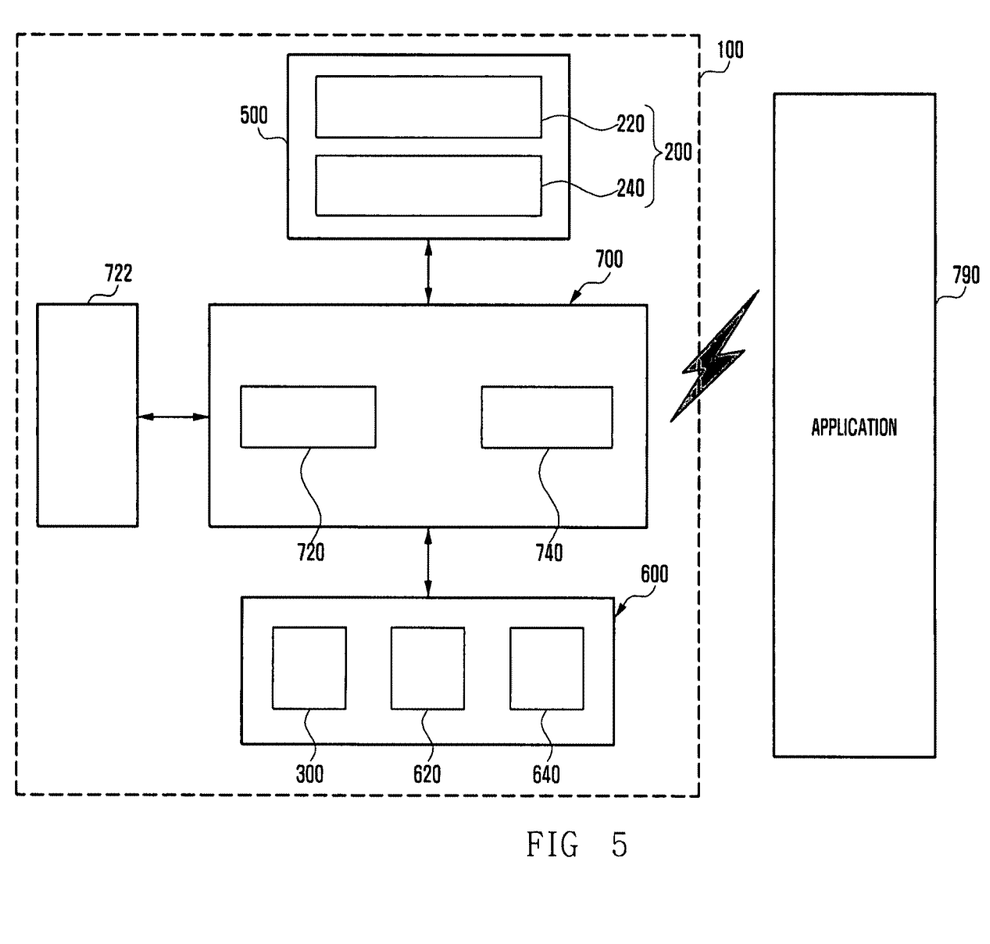
FIG. 5 is a block diagram illustrating an electronic device having a user identification function according to various embodiments of the present disclosure.

The electronic device 100 may include an ECG sensor 200 (as shown in FIG. 5) for identifying the user, and a heart rate monitor (HRM) sensor, or HRM sensor 300 for detecting a wearing state of the electronic device by the user.

The ECG sensor 200 may include a first identification sensor 220 that is operated when user authentication is desired, and a second identification sensor 240 that is attached to a wrist of the user. For example, the first identification sensor 220 may be in the form of a button on an upper surface or an upper portion 154 of the body 120 and the second identification sensor 240 may be located in a lower portion or a lower surface 158 of the body 120.

The first identification sensor 220 may generate a waveform of a voltage according to an ECG pattern when the user is authenticated to perform payments and login processes, and the second identification sensor 240 may generate a waveform of a voltage according to an ECG pattern of the heart beats of the user.

The first identification sensor 220 is operated, for example, by pushing a button associated with the first identification sensor 220 for a predetermined time period, which may generate a human body communication loop.

The HRM sensor 300 may periodically detect a wearing state of the electronic device 100 by the user. For example, the HRM sensor 300 may be attached to the lower portion or the lower surface 158 of the body 120 adjacent to the second identification sensor 240, and it may be preferable to use a PPG method in which variations of reflection of light are sensed according to a flow of blood to measure heart beats or heart rates.

The buckle assembly 160 may further include a coupling detection sensor 620 (as shown in FIG. 5) that detects that a first end 162 of the opposite ends of the band 140 is coupled to a second end 166 of the opposite ends of the band 140, which enters the buckle assembly 160 into an in-use state of the electronic device 100.

The coupling detection sensor 620 may detect if the user releases the wearing (the in-use) state of the electronic device 100 thus also exiting the in-use state of the electronic device 100. For example, the electronic device 100 may include the buckle assembly 160, into which the first end 162 of the band 140 is inserted to be coupled to the buckle assembly 160 on the second end 166 such that the electronic device 100 is mounted or secured on a wrist of the user. Conversely, the electronic device 100 may use the coupling detection sensor 620, such as, for example, a general photo sensor, a magnet, or a lead switch, to detect if the user releases the band 140 from the buckle assembly 160 to exit the in-use state of the electronic device 100.

After the electronic device 100 having a user identification function, according to various embodiments of the present disclosure, is worn by the user, the user may be identified by comparing ECG patterns according to waveforms of the voltages detected through the first identification sensor 220 and the second identification sensor 240 of the ECG sensor 200 in order to perform a user authentication for the electronic device 100. Results of the user authentication performed may be stored in an ECG authentication storage.

As long as the user maintains the wearing state of the electronic device 100, after the user authentication has been performed through the ECG sensor 200, the electronic device 100 may achieve an authentication maintaining effect.

To achieve an authentication maintaining effect, the electronic device 100 of the present disclosure checks whether the coupling detection sensor 620, which includes the buckle assembly 160, is being kept in the wearing state, and also periodically checks the wearing state of the electronic device 100 by the user through the FIRM sensor 300.

Accordingly, the electronic device 100 of the present disclosure may continue to authenticate the user as long as the user wears the electronic device 100, without using a separate user identification means. It may also be unnecessary to perform ECG sensing again whenever the authentication is performed.

Figure 4:
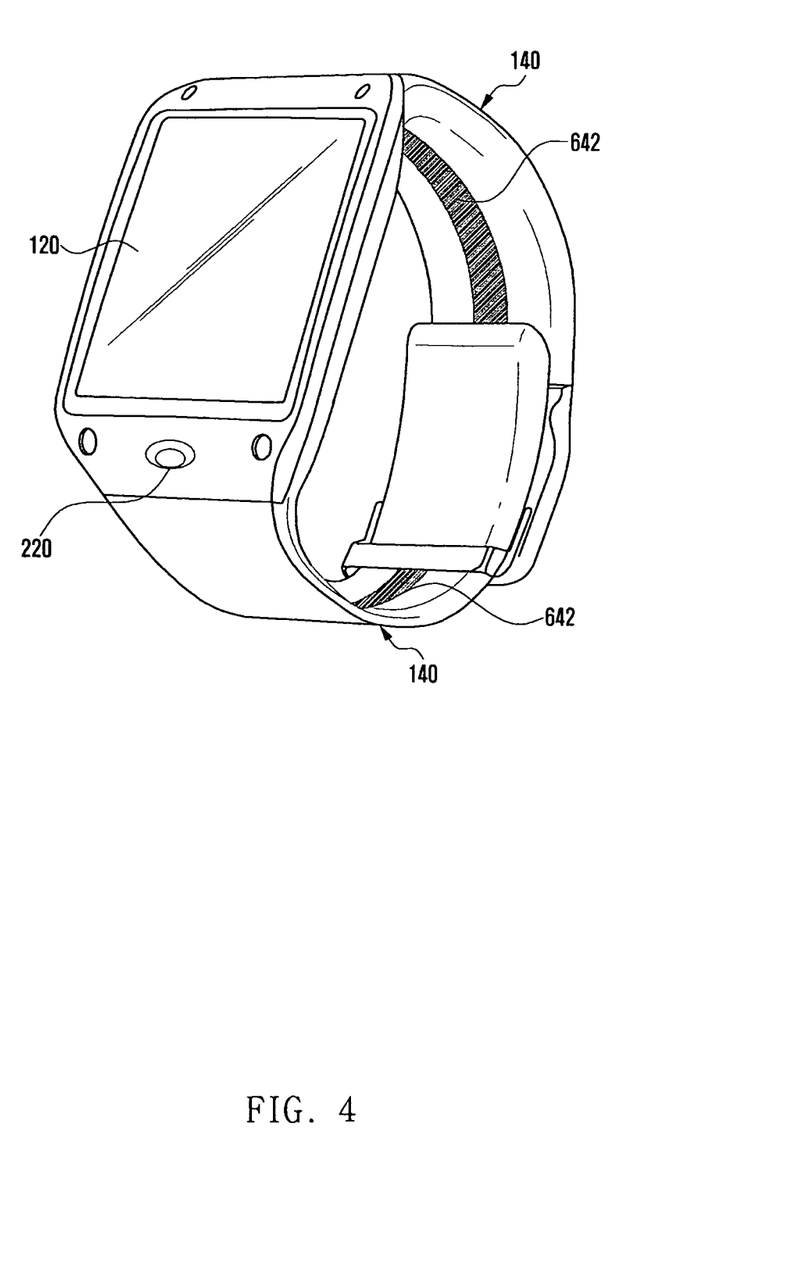
FIG. 4 is a schematic diagram illustrating a band of an electronic device according to various embodiments of the present disclosure.

FIG. 4 illustrates the band 140 of the electronic device 100 according to various embodiments of the present disclosure.

Referring to FIG. 4, the band 140 of the electronic device 100 may further include a tamperproof or wrongful use prevention sensor 640 (shown in FIG. 5) that may prevent the wrongful use of the electronic device 100, on which an authentication has already been performed. For example, if the electronic device 100, on which an authentication of the user has been performed, is used after the band 140 of the electronic device 100 is cut off by a third person, the third person may wrongfully use the electronic device 100 without performing ECG sensing again because the electronic device 100 may be stolen without permission while the wearing state of the electronic device 100 based on the coupling detection sensor 620 has not been reset by the user.

In order to provide such a tamperproof function, the wrongful use prevention sensor 640 may include a conductive body 642 that is embedded in the band 140 in the shape of a stripe.

According to an embodiment of the present disclosure, because the conductive body 642 is also cut off if a third person cuts off the band 140, a processor 700 (as shown in FIG. 5) may detect a sign of wrongful use accordingly, and then the wrongful use by the third person may be prevented by commanding the elimination or discarding of ECG authentication information of the user that is stored in a security memory 720 (as shown in FIG. 5) in the processor 700.

FIG. 5 illustrates the electronic device 100 having a user identification function according to various embodiments of the present disclosure.

Referring to FIG. 5, the electronic device 100 having a user identification function, according to the present disclosure, may include the body 120 (e.g., as shown in FIG. 4), a user identification unit 500 that detects a body signal of the user and performs an authentication of the user of the electronic device 100, an in-use detection unit 600 that detects a body signal of the user and checks an in-use state of the electronic device 100 by the user, and a processor 700 that authenticates the user according to a detection signal of the user identification unit 500.

The user identification unit 500 may include an ECG sensor 200 for identifying the user, and the in-use detection unit 600 may include an HRM sensor 300 for detecting a wearing state of the electronic device 100 by the user, as described above.

The processor 700 compares ECG patterns according to waveforms of voltages detected through the first identification sensor 220 and the second identification sensor 240

(acting as a pair of ECG sensors) of the user identification unit 500 using an ECG pattern analysis solution 740 to yield in a comparison result. The processor 700 also authenticates the user of the electronic device 100 by identifying the user according to the comparison result.

The processor 700 may include a security memory 720 that stores and preserves authentication contents of the user through ECG sensing.

When the user does not release the wearing state of the electronic device 100 after the user is authenticated (ECG authentication) through ECG sensing, the processed user authentication information may be stored in the security memory 720 in the processor 700, which is an ECG authentication storage.

The electronic device 100, according to various embodiments of the present disclosure, may identify the wearing state of the electronic device 100 by the user according to a signal of the coupling detection sensor 620.

Furthermore, because the coupling detection sensor 620 detects the wearing state of the electronic device 100, and the FIRM sensor 300 of the in-use detection unit 600 periodically monitors the wearing state of the electronic device 100, the processor 700 may command the security memory 720 in the processor 700 to eliminate or discard ECG authentication information that is stored and preserved in the security memory 720 according to a detection signal of the coupling detection sensor 400 or the in-use detection unit 600 when the electronic device 100 is taken off from the user.

In another embodiment, ECG authentication information may be stored in an external memory 722 external to the processor 700. In such embodiments, the security memory 720 is embedded in the processor 700.

If the wearing state of the electronic device 100 is not released, but the user continues to wear the electronic device 100, the processed ECG authentication is available and may be used in various authentication procedures.

Differently, because the ECG authentication information stored in the security memory 720 or the external memory 722 is eliminated or discarded, automatically or selectively, if the wearing state of the electronic device 100 is released or the electronic device 100 is not worn, the electronic device 100 may prompt for a new ECG authentication procedure.

Furthermore, even though a third person cuts off the band 140 for the purpose of theft while the wearing state of the electronic device 100 is not released, the wrongful use by a third person can be prevented because the processor commands the security memory 720 or the external memory 722 to eliminate or discard, automatically or selectively, the ECG authentication information stored in the security memory 720 or the external memory 722 according to a detection signal of the wrongful use prevention sensor 640 for detecting a sign of a wrongful use of the electronic device 100 by cutting-off the conductive body 642 in the band 140.

Figure 6:
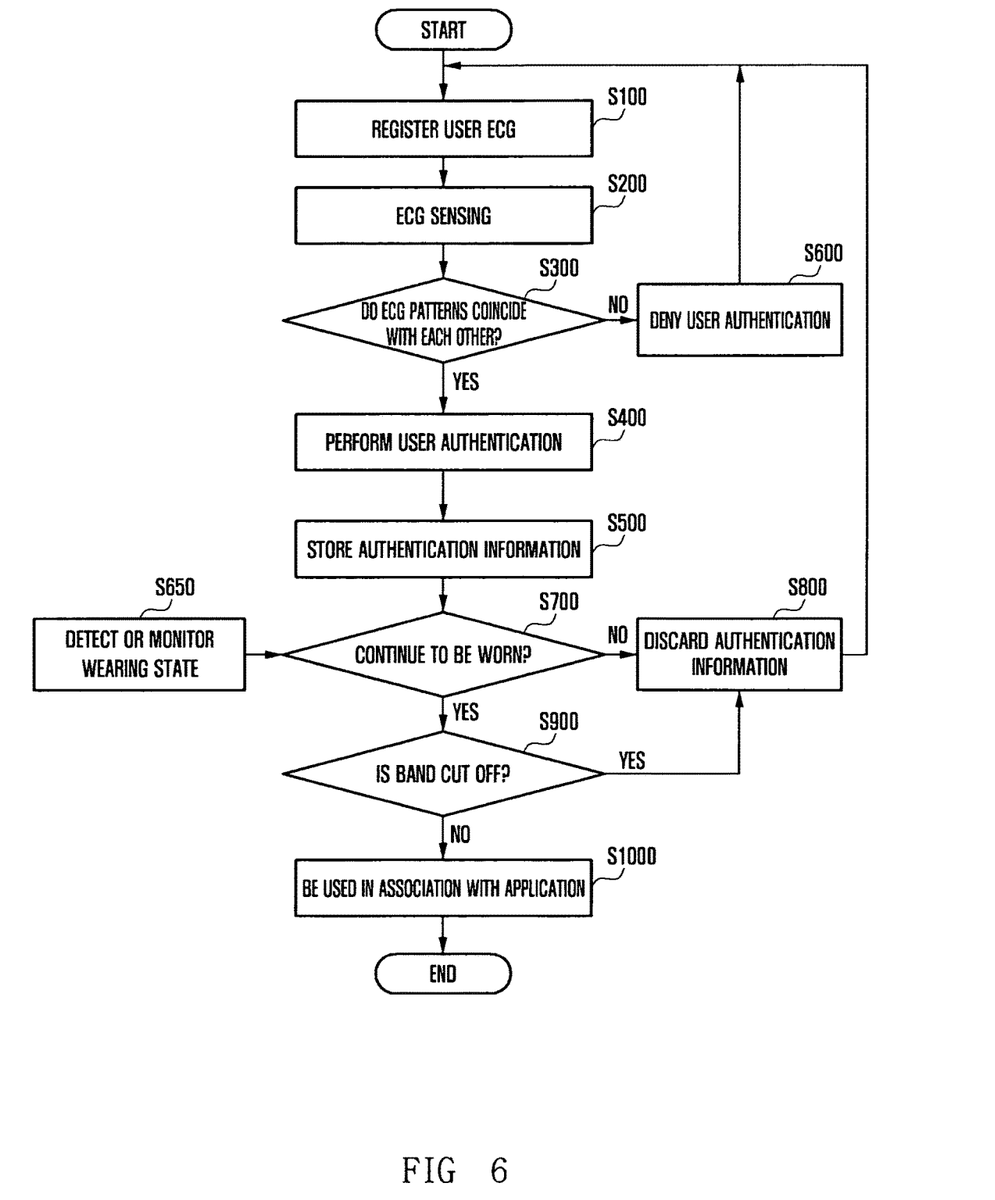
FIG. 6 is a flowchart illustrating an operation of an electronic device having a user identification function according to various embodiments of the present disclosure.

A user authentication procedure of the electronic device 100 having a user identification function, according to the present disclosure, will be described with reference to FIG. 6.

First, an authentication registering step (S100) of registering an ECG pattern of the user is performed before the user puts on the electronic device 100.

Next, while the user wears the electronic device 100 such that the second identification sensor 240 (of FIG. 2) is placed onto a wrist of the user, ECG sensing at S200 is started by pushing or touching the first identification sensor 220 (of FIG. 1) at the upper portion 154 (of FIG. 1) of the body 120 for a predetermined time period (as shown in FIG. 3).

In S300, the processor 700 (of FIG. 5) records waveforms detected by electrodes of the first identification sensor 220 and the second identification sensor 240, and identifies the user by comparing the waveforms detected with the ECG pattern of the user (of S100), which has been registered in advance, by using an ECG pattern analysis solution 740.

If the ECG pattern of the user coincides with the ECG pattern of the registrant in the identification result, as determined in S300, user authentication is performed in S400, and the authentication information is stored in the security memory 720 in the processor 700 or the external memory 722 in S500. If the ECG pattern of the user does not coincide with the ECG pattern of the registrant in the identification result, as determined in S300, authentication is denied and the user is considered an non-registrant in S600.

In S700, whether the user continues to wear the electronic device 100 is checked. Specifically, the processor 700 detects the wearing state of the electronic device 100 with the coupling detection sensor 620 and continuously monitors the wearing state of the electronic device 100 via the HRM sensor 300, as shown in S650. The authentication information stored in the security memory 720 or the external memory 722 is eliminated or discarded, automatically or selectively, if the electronic device 100 is released or not mounted or worn in S800. Thereafter, accordingly, the user may perform a new user authentication operation, thus repeating S100.

Differently, if the user continues to wear the electronic device 100, the ECG authentication is available and accordingly, may be variously used in association with applications in S1000.

According to an embodiment of the present disclosure, in S900, the processor 700 checks whether the conductive body 642 of the band 140 is cut off through a detection signal of the wrongful use prevention sensor 640 even though the user continues to wear the electronic device 100. The processor 700 also may eliminate or discard, automatically or selectively, the ECG authentication information stored in the security memory 720 or the external memory 722 in S800, if it is determined that the band 140 is cut off in S900. Otherwise, the processor 700 may in S1000 variously use the ECG authentication in association with an application 790 (of FIG. 5) because the ECG authentication remains to be available if it is identified that the user continues to wear the electronic device 100 while the band 140 is not cut off.

Figure 7:
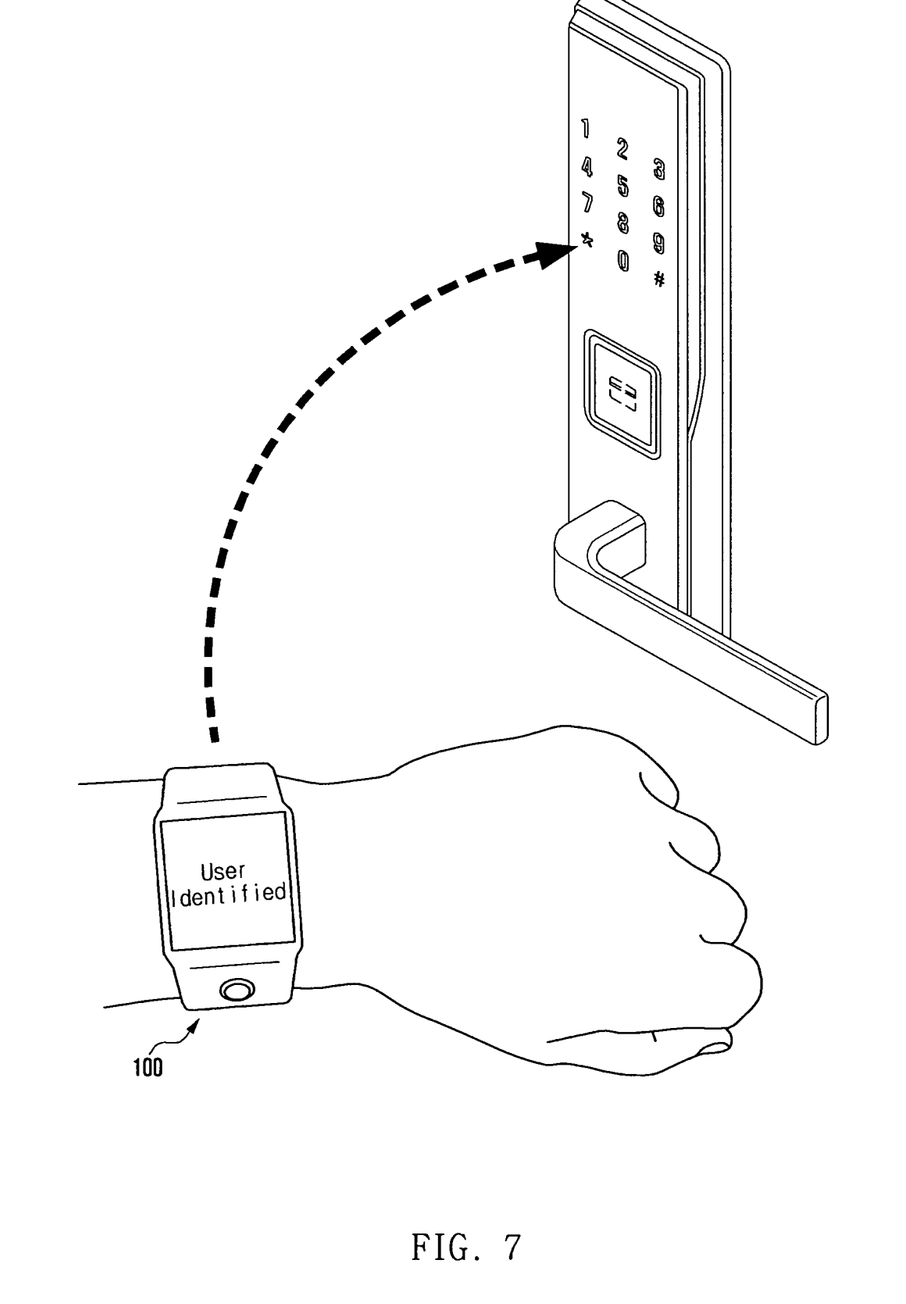
FIG. 7 is a view illustrating an example of automatically releasing a door lock through ECG authentication of an electronic device having a user identification function according to various embodiments of the present disclosure.
Figure 8:
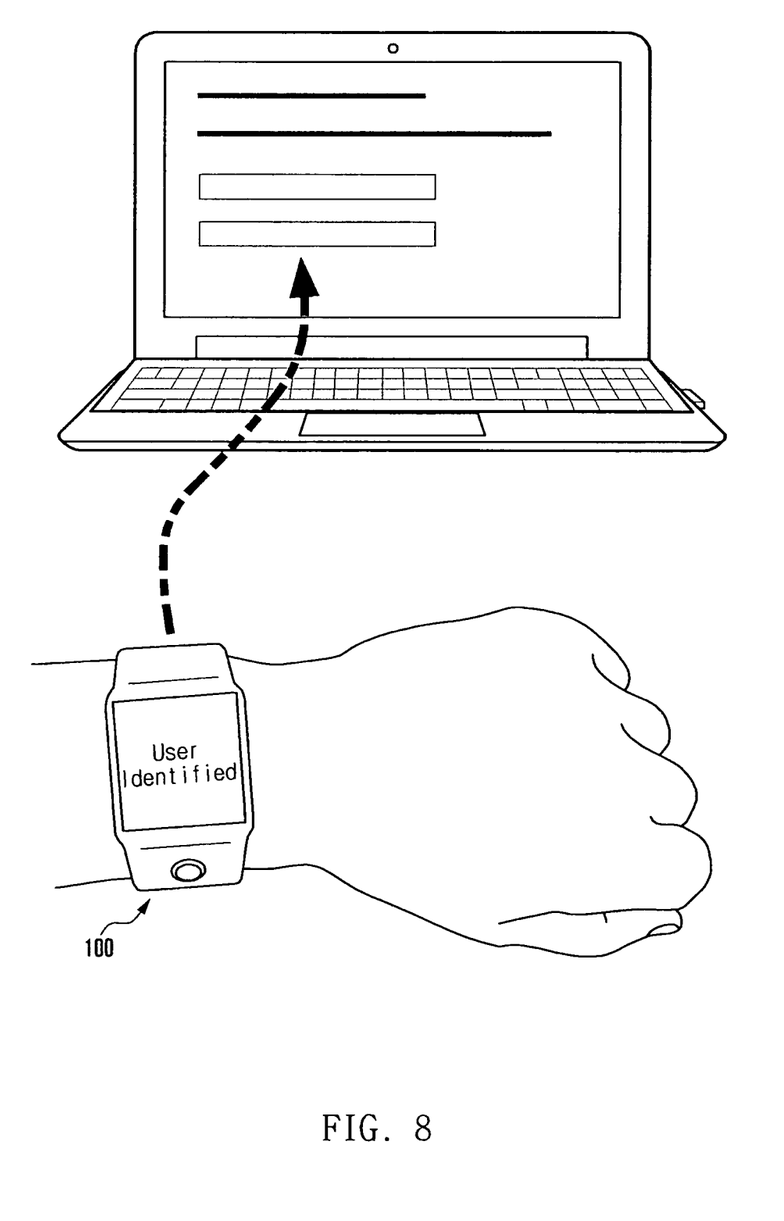
FIG. 8 is a view illustrating an example of an automatic login through ECG authentication of an electronic device having a user identification function according to various embodiments of the present disclosure.

FIGS. 7 and 8 exemplify a process of automatically releasing a door lock through an ECG authentication of the electronic device 100 having a user identification function according to an embodiment of the present disclosure, and an application (e.g., the application 790 of FIG. 5) for the automatic login of a PC or a smartphone.

Referring to FIGS. 7 and 8, if the user continues to wear the electronic device 100, the user may enter a building without inputting a separate key or a password using the user authentication information stored in the security memory 720 or the external memory 722, and may automatically log in a PC or a smartphone by linking the user authentication information to a terminal or a service through Bluetooth or Wi-Fi Direct.

Furthermore, although not exemplified in detail, an application associated with an ECG authentication may unlock a vehicle without using a separate smart key, may open a safe without inputting a separate key or a password, may immediately perform a payment without a separate approval through a Point-Of-Sales (POS) or the like, and may be applied to other various applications.

As described above, according to various embodiments of the present disclosure, because a user identifying ECG sensor and a wearing state detecting FIRM sensor are simultaneously mounted, an authentication may be made as long as the user wears the electronic device through the user identifying ECG sensor without using a separate user identifying means, and an authentication effect can be maintained through the wearing state detecting HRM sensor.

In addition, through the fact that the user is not changed as long as the user does not release the wearing state, the user authentication can continue the authentication effect and can be associated with various applications such as a PC, a smartphone, a door lock, a vehicle, a safe, a payment, and the like without an additional user authentication.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device for use with a user, the electronic device comprising:
    a band comprising a first end and a second end, the band configured to secure the electronic device on the user when the first end is coupled to the second end;
    a user identification device configured to:
        detect a body signal of the user, and
        generate an authentication signal of the user to be transmitted from the electronic device to an external device;
    an in-use detection device configured to determine whether the user uses the electronic device, the in-use detection device comprising a coupling detection sensor and a heart rate monitor (HRM) sensor;
    at least one processor configured to:
        authenticate the user according to the body signal detected by the user identification device,
        transmit the authentication signal from the electronic device to the external device,
        based on the user being authenticated by the user identification device, determine the electronic device is being worn by detecting that the first end of the band is coupled to the second end of the band and the HRM sensor detecting that the user wears the electronic device,
        based on the determination that the electronic device is being worn, determine that the band has not been cut, and
        based on the determination that the while the electronic device is being worn the band has not been cut, operate an application on the electronic device in association with the authentication signal; and
    a memory configured to store authentication information of the user authenticated by the at least one processor,
    wherein the at least one processor is further configured to eliminate at least a portion of the authentication information of the user stored in the memory in response to the coupling detection sensor detecting that the first end of the band is not coupled to the second end of the band or the HRM sensor detecting that the user is not wearing the electronic device.

2. The electronic device of claim 1, wherein the user identification device comprises an electrocardiogram (ECG) sensor that identifies the user through ECG sensing.

3. The electronic device of claim 2, further comprising:
    a body,
    wherein the ECG sensor comprises a first identification sensor and a second identification sensor, and
    wherein the first and second identification sensors are attached to different surfaces of the body.

4. The electronic device of claim 3,
    wherein the first identification sensor is configured to generate a waveform according to an ECG pattern of heartbeats of the user, and
    wherein the second identification sensor is configured to generate a waveform according to an ECG pattern when the user makes various payments or performs an authentication in a login process.

5. The electronic device of claim 4, wherein the first identification sensor is located in a button on the body to be operated by pushing the button, and completes a human body communication loop.

6. The electronic device of claim 1, wherein the HRM sensor is configured to detect a wearing state of the electronic device by the user in a photoplethysmography (PPG) method.

7. The electronic device of claim 1, wherein the at least one processor is further configured to:
    record a waveform detected through the user identification device,
    compare the waveform with an ECG pattern of the user yielding in a comparison result, the ECG pattern being registered in advance, by using an ECG pattern analysis solution, and
    process a user authentication for the electronic device by identifying the user according to the comparison result.

8. The electronic device of claim 1, further comprising:
    a body,
    wherein the body further comprises a wrongful use prevention sensor that is located at a wearing position of the user.

9. The electronic device of claim 8, wherein the wrongful use prevention sensor is a conductive body that is embedded in a band.

10. A user authentication method for use with an electronic device having a band, the method comprising:
    registering an electrocardiogram (ECG) pattern of a user resulting in a registered ECG pattern;
    sensing an ECG pattern of the user;
    comparing the registered ECG pattern and the ECG pattern of the user sensed, and
    identifying the user;
    if the registered ECG pattern coincides with the ECG pattern of the user sensed based on the identification, authenticating the user including generating an authentication signal of the user and storing authentication information;
    checking a wearing state of a body by a coupling detection sensor detecting that a first end of the band is coupled to a second end of the band and a heart rate monitor (HRM) sensor detecting that the user wears the electronic device;
    based on the user being authenticated by the user identification device, determining the electronic device is being worn by detecting that the first end of the band is coupled to the second end of the band and the HRM sensor detecting that the user wears the electronic device;
    based on the determination that the electronic device is being worn, determine that the band has not been cut; and based on the determination that the while the electronic device is being worn the band has not been cut, transmitting the authentication signal from the electronic device to an external device and allowing an application on the electronic device to be operable in association with the authentication signal; and eliminating at least a portion of the authentication information stored in response to the coupling detection sensor detecting that the first end of the band is not coupled to the second end of the band or the HRM sensor detecting that the user is not wearing the electronic device.

11. The user authentication method of claim 10, wherein the user is identified by comparing the registered ECG pattern of the user with the ECG pattern of the user sensed using an ECG pattern analysis solution.

12. The user authentication method of claim 10, wherein when the wearing state of the body is identified, the authentication that is stored is discarded via detecting a wrongful use of the body.

* * * * *